United States Patent
Kleppe et al.

(10) Patent No.: US 8,988,771 B2
(45) Date of Patent: Mar. 24, 2015

(54) METHOD FOR EVALUATING FLUORESCENCE RESULTS IN A MICROSCOPE IMAGE

(75) Inventors: Ingo Kleppe, Jena (DE); Thomas Kalkbrenner, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 250 days.

(21) Appl. No.: 13/380,171

(22) PCT Filed: Jun. 19, 2010

(86) PCT No.: PCT/EP2010/003705
§ 371 (c)(1),
(2), (4) Date: Feb. 23, 2012

(87) PCT Pub. No.: WO2010/149319
PCT Pub. Date: Dec. 29, 2010

(65) Prior Publication Data
US 2012/0140317 A1   Jun. 7, 2012

(30) Foreign Application Priority Data
Jun. 26, 2009   (DE) .......................... 10 2009 031 231

(51) Int. Cl.
G02B 21/00   (2006.01)
G02B 21/16   (2006.01)
G01N 21/64   (2006.01)

(52) U.S. Cl.
CPC ............ G02B 21/0076 (2013.01); G02B 21/16 (2013.01); G02B 21/008 (2013.01); G01N 21/6458 (2013.01)
USPC .......................................... 359/368; 359/385

(58) Field of Classification Search
USPC ................................................. 359/368, 385
See application file for complete search history.

(56) References Cited

U.S. PATENT DOCUMENTS 5,671,085 A   9/1997   Gustafsson et al.
5,784,162 A   7/1998   Cabib et al.
(Continued)

FOREIGN PATENT DOCUMENTS

JP   05 284998   11/1993
JP   11-500832   1/1999
(Continued)

OTHER PUBLICATIONS

International Search Report for Application No. PCT/EP2010/003705 dated Aug. 25, 2010.
(Continued)

*Primary Examiner* — Frank Font
(74) *Attorney, Agent, or Firm* — Frommer Lawrence & Haug LLP

(57) ABSTRACT

The invention allows a quantitative evaluation of images acquired by microscope having fewer errors and is applicable in connection with high-resolution methods, particular at a high speed. A microscope image is analyzed in which the intensity distributions of fluorescence events have in each instance a diffraction-dependent extent which corresponds to an extent of a point spread function of the microscope and are arranged so as to be spatially non-overlapping, or at least predominantly spatially non-overlapping, in that at least one counter is initialized for every region to be analyzed in the microscope image, at least one fluorescence event is identified in a region to be analyzed in the microscope image, and the counter corresponding to the relevant region is incremented for each fluorescence event identified in the region. The counting results in a dramatic improvement in the signal-to-noise ratio at a high evaluation speed.

16 Claims, 4 Drawing Sheets

(56) References Cited

U.S. PATENT DOCUMENTS

| | | | |
|---|---|---|---|
| 6,007,996 | A | 12/1999 | McNamara et al. |
| 6,909,105 | B1 | 6/2005 | Heintzmann et al. |
| 7,342,717 | B1 * | 3/2008 | Hausmann et al. ........... 359/370 |
| 7,365,344 | B2 | 4/2008 | Aoki |
| 7,535,012 | B2 | 5/2009 | Betzig et al. |
| 7,626,694 | B2 | 12/2009 | Betzig et al. |
| 7,626,695 | B2 | 12/2009 | Betzig et al. |
| 7,626,703 | B2 | 12/2009 | Betzig et al. |
| 7,710,563 | B2 | 5/2010 | Betzig et al. |
| 7,782,457 | B2 | 8/2010 | Betzig et al. |
| 7,864,314 | B2 | 1/2011 | Betzig et al. |
| 7,916,304 | B2 | 3/2011 | Hess |
| 8,000,509 | B2 | 8/2011 | Zhu et al. |
| 8,462,336 | B2 | 6/2013 | Betzig et al. |
| 8,599,376 | B2 | 12/2013 | Betzig et al. |
| 8,693,742 | B2 * | 4/2014 | Piestun et al. ................ 382/128 |
| 2005/0024637 | A1 | 2/2005 | Olschewski |
| 2005/0224721 | A1 | 10/2005 | Aoki |
| 2005/0270639 | A1 * | 12/2005 | Miki ............................. 359/381 |
| 2008/0068588 | A1 | 3/2008 | Hess et al. |
| 2008/0068589 | A1 | 3/2008 | Hess et al. |
| 2008/0070322 | A1 | 3/2008 | Hess et al. |
| 2008/0070323 | A1 | 3/2008 | Hess et al. |
| 2008/0111086 | A1 | 5/2008 | Betzig et al. |
| 2008/0158551 | A1 | 7/2008 | Hess |
| 2008/0212172 | A1 * | 9/2008 | Zhu et al. ...................... 359/383 |
| 2008/0212865 | A1 | 9/2008 | Zhu et al. |
| 2009/0086204 | A1 * | 4/2009 | Maiti et al. .................... 356/317 |
| 2009/0134342 | A1 | 5/2009 | Hell et al. |
| 2009/0206251 | A1 | 8/2009 | Hess et al. |
| 2009/0237501 | A1 | 9/2009 | Lemmer et al. |
| 2010/0181497 | A1 | 7/2010 | Hess et al. |
| 2011/0081653 | A1 | 4/2011 | Hell et al. |
| 2011/0102787 | A1 | 5/2011 | Hess et al. |
| 2011/0170200 | A1 | 7/2011 | Hess |
| 2011/0174986 | A1 | 7/2011 | Kempe et al. |
| 2011/0194174 | A1 * | 8/2011 | Laudo .......................... 359/385 |
| 2011/0226965 | A1 | 9/2011 | Wolleschensky et al. |
| 2011/0284767 | A1 | 11/2011 | Wolleschensky et al. |
| 2011/0317904 | A1 | 12/2011 | Zhu et al. |
| 2013/0126759 | A1 | 5/2013 | Betzig et al. |

FOREIGN PATENT DOCUMENTS

| | | |
|---|---|---|
| JP | 2005-043278 | 2/2005 |
| JP | 2005-055429 | 3/2005 |
| JP | 2005-300310 | 10/2005 |
| JP | 2008-542826 | 11/2008 |
| JP | 2010-500573 | 1/2010 |
| JP | 2010-515084 | 5/2010 |
| WO | WO 97/21979 | 6/1997 |
| WO | WO 2006/127692 | 11/2006 |
| WO | WO 2008/019299 | 2/2008 |
| WO | WO 2008/080032 | 7/2008 |

OTHER PUBLICATIONS

Kenneth R Castleman et al; "Fish Image Analysis"; IEEE Engineering in Medicine and Biology Magazine, IEEE Service center, Piscataway, NJ, US, vol. 15, No. 1, Jan. 1, 1996, pp. 67-115, XP011084670 ISSN: 0739-5175.

Zhenefei Tai et al: "Automatic Fluorescent Dot Counting in Interphase Cell Nuclei using Basis Pursuit Image Analysis"; Region 5 Conference, 2008 IEEE, IEEE, Piscataway, NJ, USA, Apr. 17, 2008, pp. 1-4, XP031285295; ISBN: 978-1-4224-2076-6.

Netten H Et al: "Automation of Fluorescent dot counting in cell nuclei" Pattern Recognition, 1994. vol. 1—Conference A: Computer Vision & Image Processing; Proceedings of the 12$^{th}$ IAPR International Conference on Jerusalem, Israel Oct. 9-13, 1994. Los Alamitos, CA, USA, IEE Comput. Soc. LNKD-DOI: 10.1109/ICPR. 1194.5762, vol. 1, Oct. 9, 1994, pp. 84-87, XP010215997 ISBN:978-0-08186-6265-2.

Notification of Translation of the International Preliminary Report on Patentability dated Jan. 26, 2012, International Bureau of WIPO, Switzerland.

Notification of Reasons for Rejection an English translation for JP Patent Application No. 2012-516561 dated Apr. 8, 2014.

Eric Betzig et al., *Imaging Intracellular Fluorescent Proteins at Nanometer Resolution*, SCIENCEXPRESS REPORT, www.sciencexpress.org, p. 1-9 (Aug. 10, 2006).

Eric Betzig et al., Supporting Online Material for "Imaging Intracellular Fluorescent Proteins at Nanometer Resolution", published on Science Express, p. 1-30 (Aug. 10, 2006).

Eric Betzig, et al., *Imaging Intracellular Fluorescent Proteins at Nanometer Resolution*, 313 Science 1642-1645, www.sciencemag.org (Sep. 15, 2006).

Alexander Egner et al., *Fluorescence Nanoscopy in Whole Cells by Asynchronous Localization of Photoswitching Emitters*, 93 Biophysical J. 3285-3290 (Nov. 2007).

Michael J. Rust et al., *Sub-Diffraction-Limit Imaging by Stochastic Optical Reconstruction Microscopy (STORM)*, Nature Methods, http://www.nature.com/naturemethods, p. 1-3 (Aug. 9, 2006).

Samuel T. Hess et al., *Dynamic Clustered Distribution of Hemagglutinin Resolved at 40 nm in Living Cell Membranes Discriminates Between Raft Theories*, 104 Proceedings National Academy Sciences U.S. 17370-17375, www.pnas.org/cgi/doi/10.1073/pnas.0708066104 (Oct. 30, 2007).

Samuel T. Hess et al., *Ultra-High Resolution Imaging by Fluorescence Photoactivation Localization Microscopy*, 91 Biophysical J. 4258-4272 (Dec. 2006).

Hari Shroff et al., *Dual-Color Superresolution Imaging of Genetically Expressed Probes Within Individual Adhesion Complexes*, 104 Proceedings National Academy Sciences U.S. 20308-20313, www.pnas.org/cgi/doi/10.1073/pnas.0710517105, (Dec. 18, 2007).

* cited by examiner

METHOD FOR EVALUATING FLUORESCENCE RESULTS IN A MICROSCOPE IMAGE

The present application claims priority from PCT Patent Application No. PCT/EP2010/003705 filed on Jun. 19, 2010, which claims priority from German Patent Application No. DE 10 2009 031 231.5 filed on Jun. 26, 2009, the disclosures of which are incorporated herein by reference in their entirety.

BACKGROUND OF THE INVENTION

1. Field of the Invention

The invention is directed to methods for analyzing a microscope image comprising a plurality of picture elements, the intensity distributions of florescence events of a sample labeled with one or more types of fluorophores, and microscopes for implementing methods of this kind.

2. Description of Related Art

Research fields such as system biology which aim to describe biological systems by quantitative models rely on quantitative data. Such data could be determined heretofore only with poor accuracy by means of fluorescence microscopy, for example, by means of a "flying spot" microscope (Pawley, "Biological Confocal Microscopy", Springer Verlag, 3rd edition 2006, page 6) or by calcium imaging (Pawley, page 529) because a large number of error sources and noise sources leads to fluctuations in intensity. Examples of error sources include the large variance in the Poisson distribution for fluorescence events, uncertainty about the size of the microscope detection volume, detector noise, photophysical properties such as quantum efficiency, excitation and efficiency spectra, and the bleaching behavior of the fluorophores. Other uncertainties include differences between different types of fluorophores, inhomogeneities in illumination, and background fluorescence and autofluorescence in the sample. These errors become larger (or more important) the smaller the volumes under examination and, therefore, the smaller the quantity of molecules examined and the higher the spatial resolving power of the microscope.

However, a high resolving power of the microscope being used is required for high spatial accuracy. The resolving power depends upon the so-called point spread function (PSF) of the microscope objective which always has a finite width (spatially, a finite volume) owing to the diffraction of the light received from the sample in the microscope objective, so that a point light source such as a fluorescing molecule is optically imaged on a finite surface. Therefore, the resolving power of a microscope is inherently limited (Abbe, 1873). However, a number of approaches are known from the prior art for generating images of a higher resolution than that allowed by these inherent limits (hereinafter referred to as high resolution).

For example, through a structured illumination of the sample in a variety of phase positions (structured illumination microscopy or SIM), the maximum resolving power can be improved laterally and axially approximately by a factor of two, or even more when combined with nonlinear excitation (saturated pattern excitation microscopy or SPEM). For this purpose, a result image of correspondingly higher resolution must be reconstructed computationally from the individual images recorded successively at the phase positions. SIM is disclosed, for example, in U.S. Pat. No. 5,671,085. SPEM is disclosed, for example, in U.S. Pat. No. 6,909,105.

The use of photoswitchable fluorescent dyes to increase resolving power (photoactivated localization microscopy; PALM or PAL-M) is known from WO 2006/127692 A2. An extremely small quantity of randomly distributed fluorescent dye molecules (fluorophores) is transformed (activated) to an excitable state by light of very low intensity at an activation wavelength and is subsequently excited to fluorescence in a known manner by light in an excitation wavelength. The rest of the fluorophores which are not activated cannot be excited to fluorescence by the excitation wavelength. Owing to the random distribution, the activated and excited fluorophores generally lie far enough apart from one another spatially so that there is no mutual overlapping of the intensity distributions of the point source images, which intensity distributions arise from the fluorescence events and are widened in a diffraction-limited manner. This is also true in particular for a projection on a two-dimensional image in which the intensity distributions inevitably extend over a plurality of picture elements (pixels) because of the diffraction widening. In PAL, microscopy, a multitude of individual images are acquired, each having a small quantity of generally non-overlapping fluorescence events. in so doing, the activation of a small group of fluorophores is not repeated until after the last fluorophores activated are photobleached. The origins of the individual fluorescence events are localized in the individual images based on the diffraction-broadened intensity distributions by means of a compensation computation with subpixel resolution and are entered in a high-resolution result image.

Other variants of individual fluorophore localization are known which differ in their approach to isolation. In STOR microscopy (stochastic optical reconstruction microscopy, or STORM), the fluorophores are switched back to their initial state (deactivated), for example, by means of a second light source, as soon as enough photons have been recorded in an individual image. Besides this, there are also the methods of PALMIRA (PALM with independently running acquisition), FPALM (fluorescence PALM), dSTORM (direct STORM), and GSDIM (ground state depletion and individual molecule return).

Most of the known high-resolution methods have the disadvantage that determining a highly resolved result image from the series of successively acquired normal-resolution individual images is extremely computation intensive and, therefore, time-consuming. Further, analysis of the result images which are generated is generally carried out visually by a human observer. In so doing, subjective influences can result in a broad dispersion when determining physical, biological or chemical quantities.

SUMMARY OF THE INVENTION

It is the object of the invention to provide methods and arrangements of the type mentioned above which allow a quantitative evaluation of images acquired by microscope with minimal error. In particular, the quantitative evaluation is possible at a high speed.

The invention is designed particularly, but not exclusively, for use with high-resolution imaging methods.

According to the invention, for a method for analyzing a microscope image containing intensity distributions of fluorescence events of a sample, a microscope image is analyzed in which the intensity distributions of the fluorescence events have in each instance a diffraction-dependent extent which corresponds to an extent of a point spread function of the microscope and are arranged so as to be spatially non-overlapping, or at least predominantly spatially non-overlapping, in that the following steps are carried out:

a) at least one counter is initialized for every region of the microscope image that is specified as a region to be analyzed;

b) at least one fluorescence event is identified in a region of the microscope image that is specified as a region to be analyzed;

c) the counter corresponding to the relevant region is incremented for each fluorescence event identified in the region.

The core of the invention consists in that, instead of the time-consuming computation of fluorescence intensities to form a high-resolution result image, individual non-overlapping fluorescence events in the image to be analyzed are counted in a spatially resolved manner, in which respect the invention differs from PALM. This may be regarded as a digitalization of the microscope image with a spatial resolution which is defined by the size of the region(s); this requires a significantly smaller quantity of fluorescence events compared to PALM. This operation can be carried out at a high speed. Thus a compensation computation for localization with subpixel accuracy can be dispensed with when the regions to be analyzed are defined with a precision of a maximum of a single pixel. While localization with subpixel accuracy is needed for regions which are defined with a higher precision, in particular less than one pixel, complicated computation for forming a result image is not required. Rather, what is concerned here is merely a digitalization with a value resolution of only one bit—in this case too the spatial resolution corresponds to the size of the region(s) to be analyzed with subsequent counting. The result is the at least one counter per region as a scalar with high precision for the quantity of fluorophores or sample molecules labeled with the latter.

The regions can be specified, for example, in the form of geometric descriptions, for example, in coordinates of the pixels of the image to be analyzed, and can correspond to regions of interest (ROI) of the sample. In particular, they can comprise one or more contiguous pixels of an image of the sample. For example, regions can be specified by indicating the coordinates of the pixels contained in a relevant region (pixel list) or the coordinates of pixels surrounding a relevant region (boundary pixels). The selection of regions by the user can be carried out particularly in a high-resolution result image (which is calculated from the individual images and displayed beforehand, for example) which generally results in region boundaries which are defined with a precision higher than one pixel of the individual images.

The inventive approach of (digital) counting of fluorescence events or molecules results in a dramatic improvement in the signal-to-noise ratio. The binary measure (presence or absence of fluorescence event/molecule) used for this technique makes the newly formed "image" appreciably more robust in the face of intensity fluctuations which can arise from a variety of causes (variance of Poisson distribution, uncertainty of the size of the detection volume, detector noise, photophysical fluorophore properties, variations between different types of fluorophores, inhomogeneities in illumination, background fluorescence and autofluorescence in the sample). The (digital) counting sharply distinguishes intensity information from concentration information.

Accordingly, information about the concentration distribution (derivable from the quantity of fluorescence events/fluorophores/molecules) is largely independent from the variability of fluorescence existing between different types of fluorophores and the sensitivity thereof to local chemical environment. The only criterion is, for example, to achieve a quantity of emitted photons which allows a (definable) threshold to be reached and, therefore, to be counted as a fluorescence event and/or molecule.

When the concentration distribution of a fluorophore covers many orders of magnitude, it is difficult to image very dark structures and very light structures simultaneously because of the limited dynamic range of actual photodetectors. By means of the method described herein, the molecules are successively imaged and counted. The dynamic range of the concentration distribution is therefore independent from the dynamic range of the detection system which can accordingly be selected in such a way as to be extremely sensitive for the detection of individual molecules. For example, EMCCD cameras at full gain typically have a dynamic range of less than 1000. At the same dynamic range of the detection system, the counters obtained according to the invention have a significantly higher dynamic range. Therefore, there is also an increase in the sensitivity of the methods compared to integrating fluorescence intensity measurements. Even compared to PALM, the invention allows higher dynamics in parts of the sample in which the fluorophore density is very high. High densities of this kind cannot be resolved in high-resolution PALM result images, which rules out a quantitative evaluation.

According to the invention, the at least one counter is read out as a quantity or concentration of molecules, fluorophores or events of the relevant region, or a false-color image is outputted based on at least two counters. In case of more than one region, an image is formed which quantitatively describes the local quantity or concentration of molecules, fluorophores or events in the sample. The values of the counters according to the invention can be used, for example, to describe quantitative models in biological systems, particularly in system biology or in all other applications in which quantitative data must be determined by microscope. The high dynamics of the method according to the invention can also be used for imaging by converting the locally determined quantities or concentrations into a false-color image with pixel sizes to be specified. In theory, a false-color image of this kind can capture a dynamic range of any size which is only still limited by the sample and no longer by the detection system.

For the microscope image which is to be analyzed, the invention requires transformation of the fluorescence of only a stochastic, sufficiently small subset of all of the fluorophores of one type contained in the sample. This is accomplished, for example, when the sample is labeled by at least one type of transformable fluorophore, in that prior to step b), particularly prior to step a), the microscope image is acquired by means of a microscope in that a subset of transformable fluorophores is first transformed into an excitable state (for example, irradiated by light of an activation wavelength) in such a way that the transformed excitable fluorophores have a lower density than that given by a reciprocal of a volume thatxis unresolvable owing to diffraction (in other words, in such a way that distances which are mostly larger than an extent of a point spread function of the microscope result between the transformed excitable fluorophores) and the sample is subsequently irradiated at least partially with excitation light by means of a light source, and fluorescent radiation emitted by the sample is imaged in a diffraction-broadened manner by means of a microscope objective and by means of a light receiver. The transformation can take place chemically or optically. The optical switching method is used, for example, in PAL microscopy. After the microscope image (or additional microscope images) is acquired the activated fluorophores can be deactivated (i.e., transformed to a non-excitable state), for example, by bleaching. A (stochastic) subset of the transformable fluorophores with a sufficiently low density can then be activated and excited again in another recording cycle.

In an advantageous manner, a correlation spectroscopy measurement and/or a Förster resonant energy transfer measurement (FRET) can be carried out on the sample in addition. Steps b) and c) can also be combined with other methods of fluorescence spectroscopy suitable for measuring properties of single molecules. Combined with fluorescence correlation spectroscopy (FCS) or raster image correlation spectroscopy (RICS), different systems (e.g., proteins) to which fluorophores are bonded can be identified, or the bond verified, by means of the diffusion constants. With adjustment of the parameters for transformation, excitation and detection (reduction of power during transformation and/or excitation; increase in the "on-time" threshold value during detection), bonded objects can be distinguished from objects freely diffusing in the cell in combination with FCS/RICS, and the respective concentration can be determined. Local bonding equilibriums can be determined in this way.

In cases where the fluorescence events proceed from different types of fluorophores, a respective counter is preferably initialized in step a) for each region to be analyzed for each type of fluorophore targeted for analysis, it is determined further in step b) that the fluorescence event corresponds to a type of fluorophore to be analyzed, and in step c) the counter corresponding to the relevant region and the relevant type of fluorophore is incremented. This allows a direct comparison of the quantities and/or concentrations of different fluorophores.

In preferred embodiments, at least two counters are used (for at least two regions to be analyzed and/or for at least two types of fluorophores to be analyzed) and a quotient between the counters is calculated and outputted as stoichiometric relationship (between two different regions for the same type of fluorophore or between two different types of fluorophore in the same region of the sample or between two different types of fluorophore in two different regions of the sample). Particularly in connection with a manual selection of regions in a high-resolution result image in advance, whether by means of PALM, SIM/SPEM or other high-resolution methods, this allows stoichiometric measurements such as, for example, the analysis of the composition of protein complexes. The improvement in the signal-to-noise ratio becomes advantageously noticeable due to the small quantities of molecules occurring in PALM. Particularly in local stoichiometric measurements with a plurality of species, quantitative determination of relative and absolute concentrations by means of fluorescence intensity measurements is made more difficult by the transfer functions of the optical system (filter efficiencies, chromatic effects, etc.) which differ for different wavelengths and which are usually not known precisely. The method according to the invention circumvents these problems again through the process of discrimination by counting. The regions to be analyzed can be referred to, for example, as stoixels (stoichiometry elements).

Generally, in an advantageous manner (e.g., in case of identical types of fluorophores for both counters), a first counter can be used for a first region and a second counter can be used for a second region different from the first, or (e.g., with identical regions for both counters) a first counter can be used for a first type of fluorophore and a second counter can be used for a second type of fluorophore different from the first. This makes possible a quantitative comparison of the two regions or types of fluorophores with high precision.

In combination with FRET, in addition to the stoichiometry of two or more species (labeled by different types of fluorophores), individual chemical bonding events between these species can be observed, counted and localized with great accuracy by observing the FRET channels.

In an advantageous embodiment form, a laser scanning microscope is used for transforming into the excitable state. In this way, activation (i.e., transformation into the excitable state) can be carried out locally (e.g., in an ROI-selective manner), and by means of the determined counter rate it is possible to proceed by way of feedback until a stable stoichiometric result is determined based on the feedback.

Steps b) and c) are preferably repeated for each microscope image for analysis of a temporal sequence of microscope images containing intensity distributions of fluorescence events of the sample, wherein the intensity distributions have, for reasons relating to diffraction, a respective extent which corresponds to an extent of a point spread function of the microscope and are arranged in each instance inside the microscope images predominantly or at least predominantly without overlapping. In so doing, the emission of a fluorophore radiating at the same location over a plurality of successive microscope images is identified as an individual fluorescence event either on the basis of the first-time occurrence of the radiation at the relevant location, and therefore on the positive-going edge of the fluorescence intensity signal, or after the end of radiation at the respective location and therefore on the negative-going edge of the fluorescence intensity signal. Accordingly, incrementing takes place only in the one microscope image in which the identification takes place (either at the positive-going fluorescence edge or at the negative-going fluorescence edge). As the result of analyzing a plurality of successive microscope images, the sample under examination is larger so that the accuracy of the quantitative evaluation is improved.

In an advantageous embodiment of the method, a counter content can be logged and the counter initialized in each instance after evaluation of a predetermined quantity of microscope images. This applies in particular to all counters. An embodiment of this kind allows a time-resolved quantitative evaluation with high precision. Accordingly, the temporal change in local concentration ratios can be measured in a spatially resolved manner and displayed.

For step b) a location of a centroid of an intensity distribution of a fluorescence event can be determined by means of a compensation computation with sub-diffraction-limited accuracy for a highly spatially resolved quantitative evaluation (region to be analyzed is smaller than a picture element of the microscope image or boundaries of a region to be analyzed are not exclusively at edges of picture elements). At normal or coarse spatial resolution (region to be analyzed corresponds to one or more contiguous picture elements of the microscope image), the identification in step b) is accomplished at high speed merely by ascertaining for at least one picture element that a predetermined intensity threshold has been exceeded. In this case, the center or a corner of the respective picture element, for example, is used as location of the fluorescence event.

The stoichiometry is limited when reversibly switching fluorophores are used because it cannot be definitely determined in borderline cases whether the same molecule is being counted again after switching off and on or whether this molecule is a different molecule in the immediate vicinity. Convertible fluorophores generally switch between fluorescence states with different emission wavelengths. In case of a fluorophore type which fluoresces reversibly in two colors, incrementing in step c) is preferably carried out only when both fluorescence colors are identified alternately at the same location in successive microscope images in a temporal sequence of microscope images. Through simultaneous detection of both wavelengths and the inventive identification with counting as described above, reversibly switching fluorophores can be distinguished from terminally bleaching fluorophores: when the on/off process correlates in both channels, the molecule in question is the same molecule. Alternatively or in addition, different instances of a reversibly switching fluorophore type can be identified based on a given minimum deviation of location.

In stoichiometry with more than one species, another difficulty arises from the possibility of different reversible switching behavior of the different fluorophores. This can take place by deliberately disabling reversibility by bleaching or by chemical means (Heilemann et al., Angew. Chem. Int. Ed. 2008, 47, 6172, and references cited therein). Of course, this also applies to samples with only one type of fluorophore.

The invention also comprises a control unit and a computer program which are designed for implementing a method according to the invention and a microscope, particularly a laser scanning microscope, having an illumination beam path with a light source for exciting at least one type of fluorescent dye in a sample, a detection beam path having a microscope objective and a light receiver arranged downstream thereof and with a control unit, mentioned above, which is connected to the light source and to the light receiver. The microscope preferably has a light source for photoswitching a fluorescent dye, this light source likewise being connected to the control unit.

In particular, the invention comprises a control unit and a computer program having a software module for initializing at least one counter per region of the microscope image, which region is targeted for analysis, a software module for identifying at least one fluorescence event in a region of the microscope image, which region is targeted for analysis, and a software module for incrementing the counter corresponding to the relevant region for each fluorescence event identified in the region.

BRIEF DESCRIPTION OF THE DRAWINGS

Identical parts have the same reference numbers in all of the drawings.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
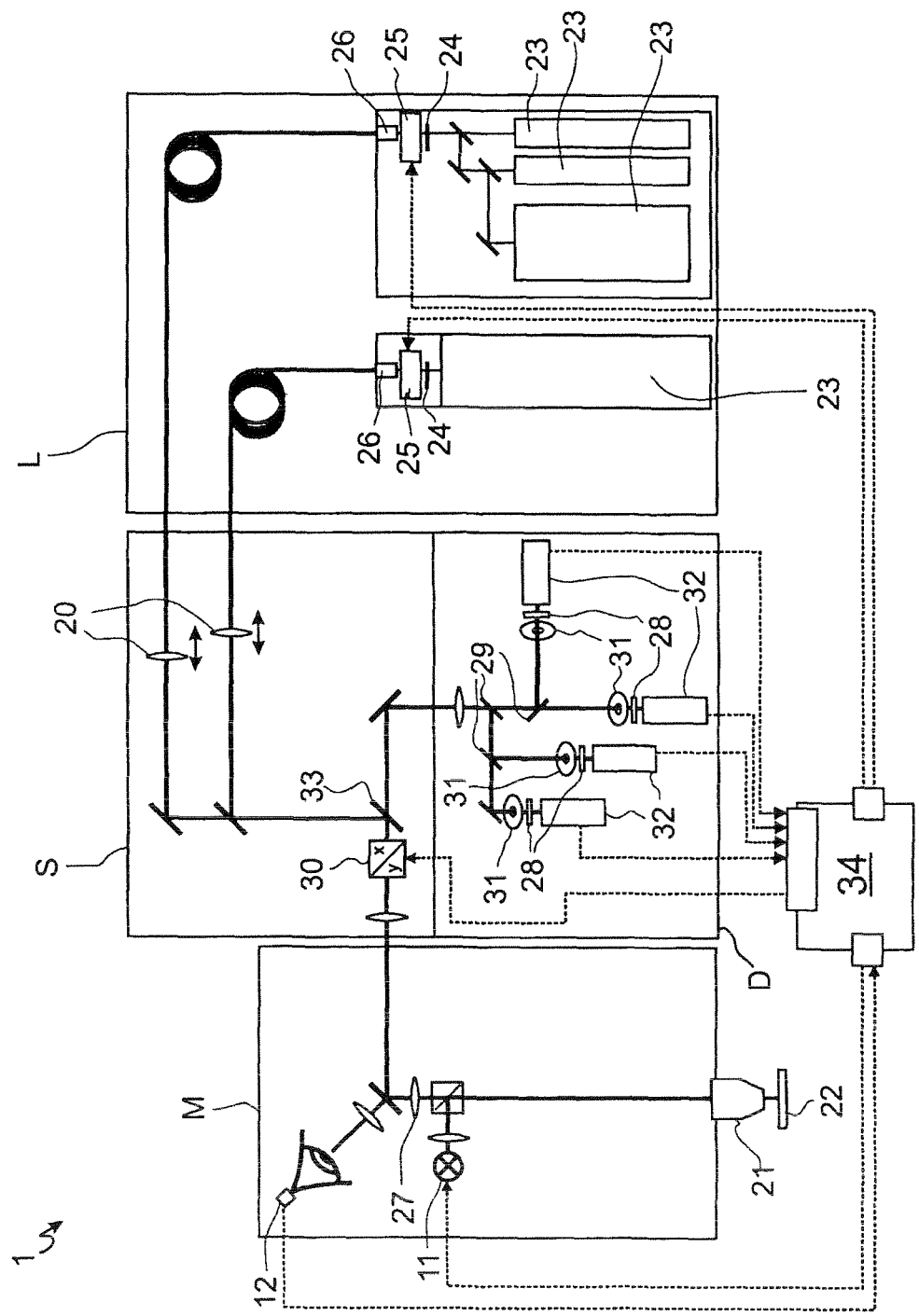
FIG. 1 shows a schematic diagram showing a microscope for the acquisition and quantitative evaluation of microscope images.

A microscope 1 having a control unit 34 designed to implement the method according to the invention is shown schematically in FIG. 1. In addition to a light source 11 and a camera 12 for widefield illumination and widefield recording of two-dimensional images, the microscope 1 is also outfitted as a laser scanning microscope (LSM). The LSM is composed modularly of an illumination module L with lasers 23, a scanning module S, a detection module D, and the microscope unit M with microscope objective 31. The light of the lasers 23 can be influenced through light flaps 24 and attenuators 25 of the control unit 34 before being fed via light-conducting fibers and coupling optics 20 into the scanning unit S and combined. The light passes via the main beamsplitter 33 and the X-Y scanning unit 30 (scanner), which has two galvanometric mirrors (not shown), through the microscope objective 21 to the sample 22, where it illuminates a focal volume (not shown). Light reflected by the sample or fluorescent light emitted by the sample passes through the microscope objective 21 to the camera 12 or via the scanning unit 30 through the main beamsplitter 30 into the detection module D. The main beamsplitter 30 can be constructed, for example, as a dichroic color splitter. The detection module D has a plurality of detection channels, each having a pinhole diaphragm 31, a filter 28, and a photomultiplier 32 which are separated by color splitters 29. Instead of pinhole diaphragms 31, for example, when using line-shaped illumination, slit diaphragms not shown) can also be used. The confocal pinhole diaphragms 31 are used to discriminate from sample light not originating from the focal volume. Therefore, the photomultipliers 32 detect exclusively light from the focal volume. The confocally illuminated and recorded focal volume of the sample 22 can be moved over the sample 22 by means of the scanning unit 30 in order to record an image pixel by pixel by rotating the galvanometer mirrors of the scanning unit 30 in a specific manner. The movement of the galvanometer mirrors as well as the switching of the illumination are controlled indirectly by the control unit 34 by means of light flaps 24 or attenuator 25. The data acquisition by the photomultipliers 32 is likewise carried out via the peripheral interface 4. Image capture by means of light source 11 and camera 12 does not depend on the adjustment of the scanning unit 30. The light source 11 can comprise two sub-light sources which are switchable by the control unit 34: a first sub-light source for activation (transformation into an excitable state) of fluorophores with an activation wavelength and a second sub-light source for excitation of these fluorophores to fluorescence.

Only one analysis unit, for example, in the form of the control unit 34 shown in the drawing, is strictly necessary for realizing the invention (analysis of existing microscope images). Further, to the extent that the microscope images are also to be acquired beforehand, the microscope unit M with light source 11 (or a plurality of light sources) and camera 12 and a control unit 34 are necessary. LSM components L, S and D are not necessary, but may be advantageous, for example, for activation and excitation in individual regions of the sample such as regions R1, R2. Correspondingly, the control unit 34 can be constructed in a simplified manner, for example, without interfaces for these components. For example, the analysis unit/control unit 34 can be a commercially available computer.

Figure 2:
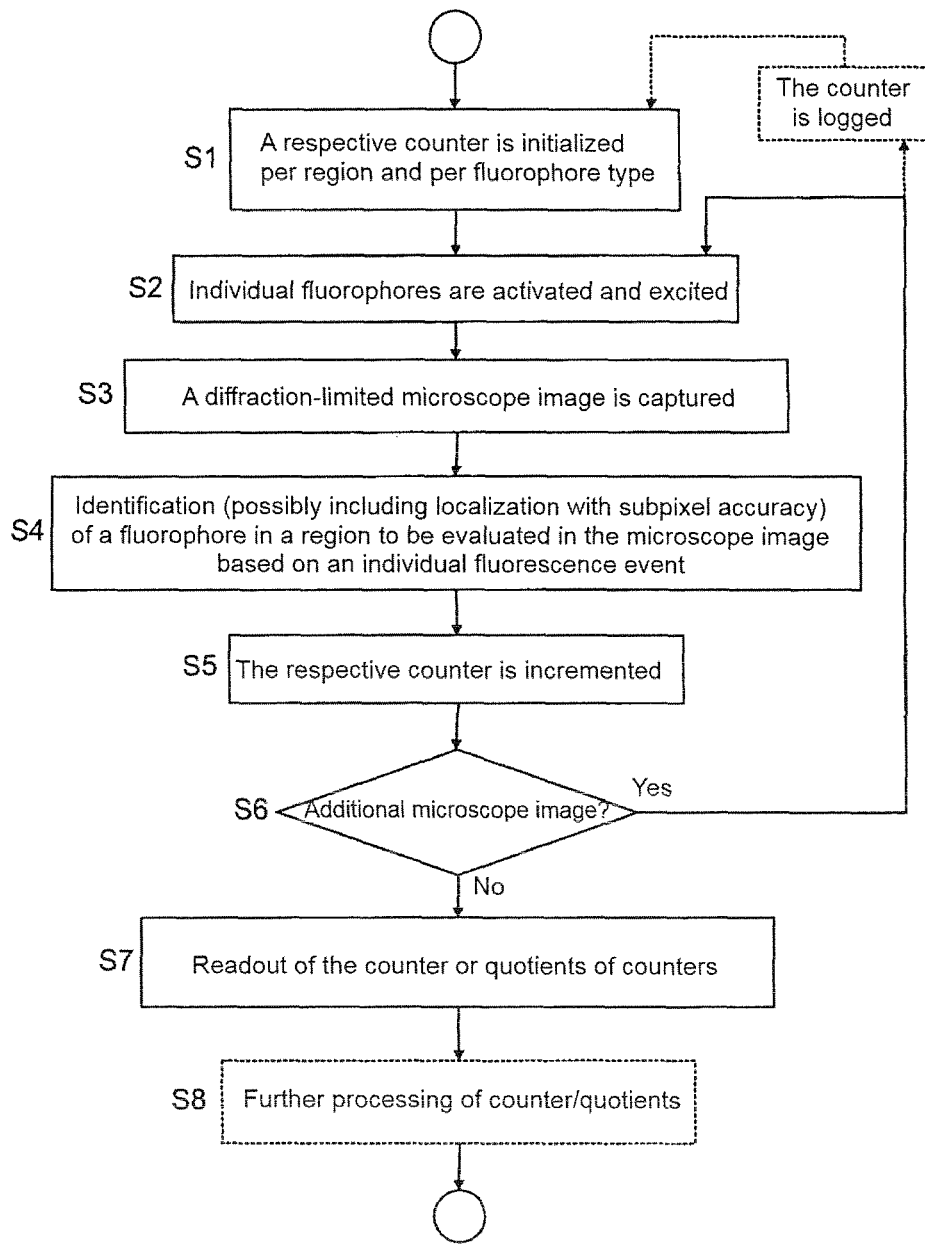
FIG. 2 shows a flowchart for a method for the quantitative evaluation of microscope images, particularly with acquisition of such images.

FIG. 2 shows a flowchart for a method according to the invention which is shown by way of example and which is carried out by means of the control unit 34 and in which the quantitative evaluation of one or more microscope images takes place immediately after the recording. It is assumed that a sample 22 which is to be analyzed and which is labeled, for example, by exactly one type of fluorophore is arranged under the objective 21 and that, for example, two regions R1, R2 (see FIG. 3) of the sample 22 are specified as regions to be analyzed. In other embodiment forms, more than one type of fluorophore and only one region or three or more regions can be analyzed. Regions R1, R2 which are shaped as circular disks purely by way of example in this instance can be specified, for example, in the form of their respective center and their radius. First, in step S1 a respective counter is initialized at zero per region R1, R2 to be analyzed (i.e., a total of two counters).

In step 2, to acquire a microscope image with a sufficiently low density of fluorescence events, only a small number of fluorophores is first transformed into their excitable state by means of light source 11 or, depending on location, by means of one of the lasers 23 through a weak flash at an activation wavelength. The selection of the subset of fluorophores which are actually activated from the total amount of all fluorophores located in the respective illumination field is carried out purely stochastically. The density of activated fluorophores is "sufficiently small" when it is less than a reciprocal of a volume that cannot be resolved by the objective 21 for reasons relating to diffraction. Subsequently, the activated fluorophores have distances from one another which are for the most part greater than an extent of the PSF of the microscope objective. The fluorophores which are transformed in this way are subsequently excited by means of an excitation wavelength differing from the activation wavelength. This can be carried out again with light source 11 or, depending upon location, with one of the lasers 23.

The fluorescent radiation which is emitted thereafter by the excited fluorophores is recorded by means of camera 12 in step S3 in a two-dimensional microscope image which is preferably stored prior to the quantitative evaluation. Owing to the diffraction of incident light in the microscope objective 21, every fluorescence event is imaged in the respective microscope image with an intensity distribution whose extent corresponds to the extent of the point spread function of the microscope objective 21 (i.e., approximately corresponding to the diameter of an Airy disk in the two-dimensional projection). Because of the distances of the activated fluorophores (predominantly greater than an extent of the PSF of the microscope objective), there is no overlapping in the intensity distributions of the fluorescence events in the microscope image.

In step S4, the individual fluorescence events are identified in the microscope image. For this purpose, the microscope image is initially processed in a known manner, for example, by means of a Gaussian filter and subsequently by means of a Laplace filter. These filters can be realized, for example, as block operators (operator matrices) which are guided over the microscope image pixel by pixel. To determine an intensity of a filtered pixel, a block operator also includes the intensities of the surrounding pixels (e.g., a block of 5×5 pixels for the Gaussian filter and a total of one block of 3×3 pixels for the Laplace filter). The Gaussian filter removes shot noise and the Laplace filter removes large contiguous areas. For identification, generally only the existence of a fluorescence event in a region is determined, not necessarily also the location within the region. This is accomplished, for example, by a sector-by-sector search for a pixel or a group of pixels with an intensity value that is greater than a given identification threshold. For example, the existence of a fluorescence event in a pixel is identified when the acquired intensity value of the respective pixel is greater than an equivalent of 50 photons.

It is only when the region to be analyzed is defined with a precision greater than that corresponding to the size of a pixel of the microscope image that, after determining the existence of a fluorescence event, a respective centroid of the intensity distribution of each fluorescence event is determined (localized) as location of the fluorescence event in question by adapting a model function, for example, a normal distribution, of the PSF to the respective intensity distribution by means of a compensation computation. Insofar as the region to be analyzed is defined only with a precision corresponding to the size of a pixel of the microscope image or with a coarser precision, localization is not required. Thus, the identification can have one step (only the existence of the fluorescence event is determined) or two steps (existence is determined and localization is carried out). For every region to be analyzed, a check is carried out as to which of the identified fluorescence events lie in the respective region. Alternatively, the identification can be carried out in such a way that only fluorescence events existing in the regions to be analyzed are searched from the start. For example, nine fluorescence events are determined in region R1 and seventeen fluorescence events are determined in region R2 as identification results.

Accordingly, in step S5 the counter for region R1 is incremented nine times and the counter for region R2 is incremented seventeen times, for example, immediately after the identification. Typically, the counters can take on any natural number and are incremented in each instance by the natural number of one. Of course, any other number amounts and a special 1-element can be used for incrementing the counters.

After a microscope image has been analyzed, it is checked in step S6 whether or not additional microscope images are to be acquired. If yes, the method continues to step S2 or if no, to step S7. In so doing, the counters are not initialized again so that further fluorescence events can be accumulated. In alternative embodiment forms (indicated by dashed lines), the instantaneous counter contents are logged (stored) and the counters are initialized so that the counter contents of any subsequences (by combining a corresponding subsequence of counter contents) or the entire image sequence can be reconstructed afterwards with low computational effort. Optionally, before reactivating a subset of fluorophores the previously activated fluorophores can be deactivated (e.g., by photobleaching or chemical bleaching.)

In step S7, the counter contents or the logs of the counter contents, if any, are outputted, for example, via a digital or analog interface. In the present instance, the quotient of the counter contents is calculated (9/17) for region R1 and for region R2 and is outputted. If the counter contents are logged in the course of acquiring serial images, a quotient can be calculated and outputted, for example, for each log entry (i.e., for each individual microscope image). The counter contents can be converted to concentration data before outputting, for example, based on the surface area or volume of the respective region.

In optional step S8, the outputted counter contents are further processed. For example, when there is a sufficiently large quantity of analyzed regions, a false-color image having a dynamic range of any size in principle can be generated and outputted. In so doing, a false color is associated respectively with an interval of counter contents and every region can be filled in with the false color in question according to a counter reading determined for it.

The method can also be applied to microscope images which have already been acquired earlier according to steps S2/S3 (S6), in which case steps S2 and S3 are omitted from the evaluation.

Figure 3:
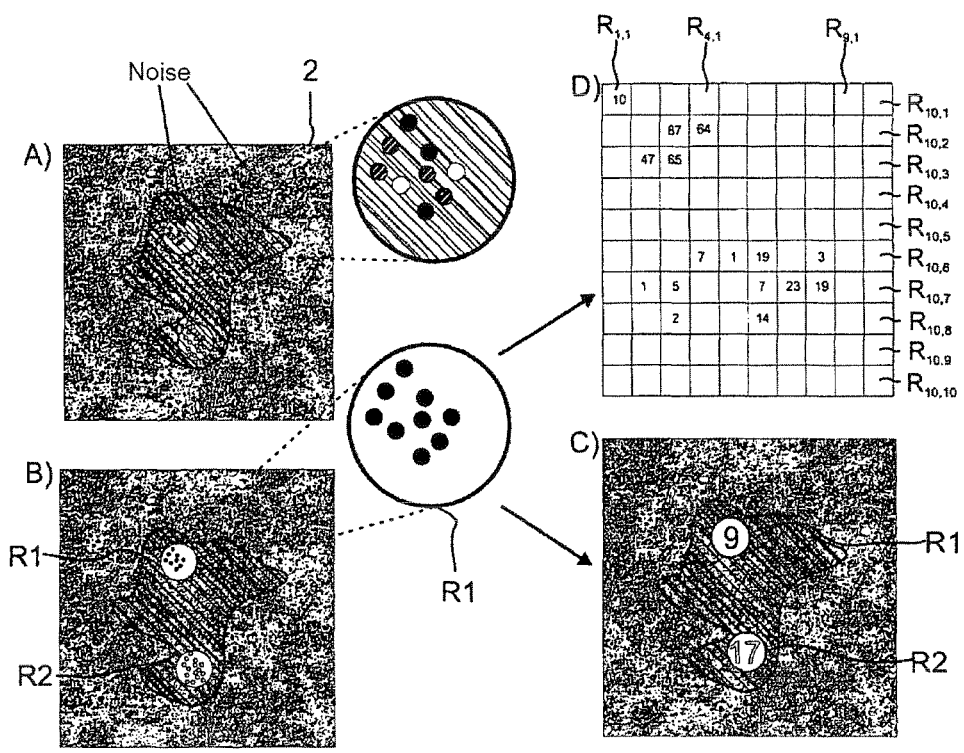
FIG. 3 shows examples of results of a quantitative evaluation for a plurality of sample regions, shown schematically.

FIG. 3 shows an example of a result of a quantitative evaluation according to the method described above. In FIG. 3A, regions R1 and R2 are shown with noisy fluorescence signals in the raw microscope image and in an enlarged section. In FIG. 3B, the individual fluorescence events identified in regions R1 and R2 after filtering the microscope image are shown in the raw microscope image and in an enlarged section. FIG. 3C shows the resulting counter contents in the regions. Accordingly, the invention makes it possible, for example, to determine the local stoichiometry between given regions and/or within given regions. FIG. 3D shows how counter contents can result for another sample with a finer resolution of the regions. The one-hundred square regions $R_{1,1}$ to $R_{10,10}$ shown by way of example directly adjoin one another. Accordingly, the invention allows the local concentration of a fluorophore to be determined in a way as an image with high contrast.

Figure 4:
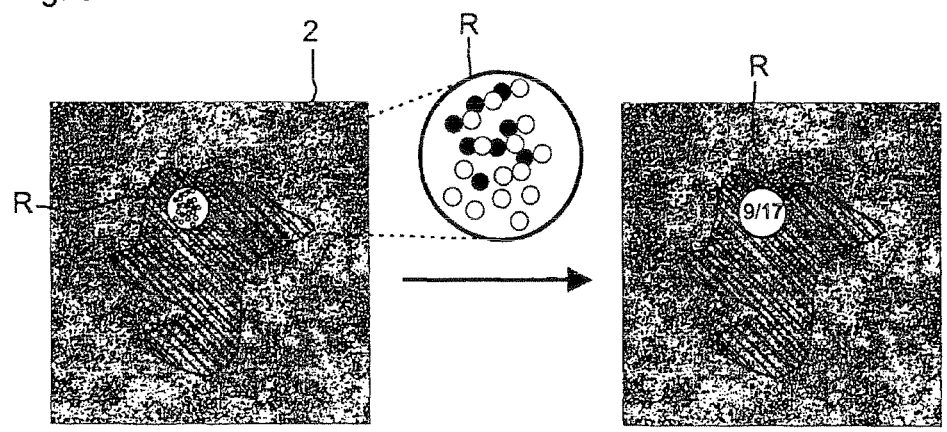
FIG. 4 shows examples of results of a quantitative evaluation for only one sample region, shown schematically.

FIG. 4 shows a result, by way of example, for a case in which only one individual sample region R labeled with two different types of fluorophore was to be analyzed. For region R, a separate counter was used for each type of fluorophore; that is, a total of two counters were used. Correspondingly, two counter contents and/or a quotient (9/17) can be outputted for region R. Accordingly, the invention makes it possible, for example, to determine the local stoichiometry also within a given region.

The quantity of counters to be used is generally given by the product of the quantity of regions to be analyzed and the quantity of fluorophore types to be analyzed.

Figure 5:
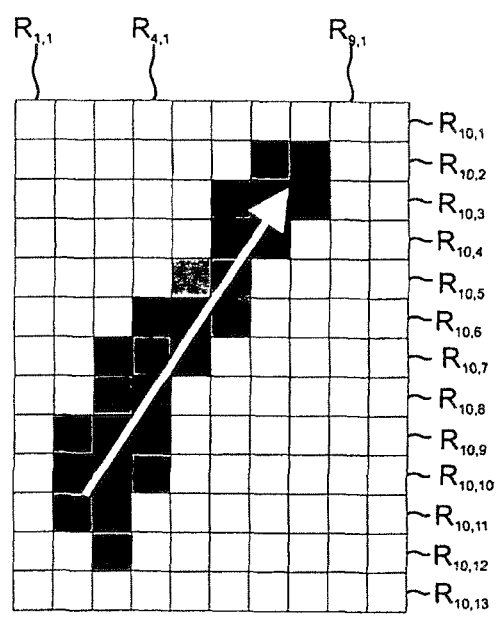
FIG. 5 shows a quantitative evaluation with temporal resolution, shown schematically.

In FIG. 5, a temporal progression of quantitative data is determined, for example, by means of logging the counter contents between individual microscope images. In so doing, the temporal resolution can be reduced by combining individual subsequences of logged counter contents subsequently. The original counter sequence advisably remains unaltered in order to allow the user to adjust the temporal resolution of the quantitative evaluation in a flexible, variable manner.

The spatial resolution can be reduced in all of the embodiment forms by combining regions (adding the respective counter contents). The counter contents of the highest-resolution original regions advisably remains unaltered in order to allow the user to adjust the spatial resolution of the quantitative evaluation in a flexible, variable manner.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMBERS 1 microscope
2 microscope image
11 light source
12 camera
20 collimating optics
21 microscope objective
22 sample
23 laser
24 light flap
25 attenuator
26 fiber coupler
27 tube lens
28 filter
29 dichroic beamsplitter
30 scanner mirror
31 pinhole diaphragm
32 photomultiplier
33 main beamsplitter
34 control unit
D detection module
M microscope
L illumination module
S scanning module
$R_{(m,n)}$ sample region

The invention claimed is:

1. A method comprising:
analyzing a microscope image containing intensity distributions of fluorescence events of a sample labeled by at least one type of transformable fluorophore, wherein the intensity distributions due to diffraction have in each instance a diffraction-dependent extent which substantially corresponds to an extent of a point spread function of a microscope and are arranged so as to be at least predominantly non-overlapping, the analysis comprising,
a) initializing at least one counter for every region of the microscope image that is specified as a region to be analyzed;
b) identifying at least one fluorescence event in a region of the microscope image that is specified as a region to be analyzed; and
c) incrementing the counter corresponding to the relevant region for each fluorescence event identified in the relevant region.

2. The method according to claim 1;
wherein the at least one counter is read out as a quantity or concentration of molecules, fluorophores, or events of the relevant region; or
wherein a false-color image is outputted based on at least two counters.

3. The method according to claim 1;
wherein at least two numerical counters are used; and
wherein a quotient between the two numerical counters is calculated and outputted as a stoichiometric relationship.

4. The method according to claim 1;
wherein the fluorescence events of the sample proceed from different types of fluorophores;
wherein a respective counter is initialized in step a) for each region to be analyzed for each type of fluorophore targeted for analysis;
wherein it is determined further in step b) that the fluorescence event corresponds to a type of fluorophore to be analyzed; and
wherein in step c) the counter corresponding to the relevant region and the relevant type of fluorophore is incremented.

5. The method according to claim1;
wherein a first counter is used for a first region and a second counter is used for a second region different from the first region.

6. The method according to claim 1;
wherein the microscope image is acquired by means of the microscope prior to step b), in that a subset of transformable fluorophores is first transformed into an excitable state in such a way that the transformed excitable fluorophores have a lower density than that given by a reciprocal of a volume that is unresolvable owing to diffraction;
wherein the sample is subsequently irradiated at least partially with excitation light by means of a light source; and wherein fluorescent radiation emitted by the sample is imaged in a diffraction-broadened-manner by means of a microscope objective and by means of a light receiver.

7. The method according to claim 1;
wherein a correlation spectroscopic measurement or a Förster resonant energy transfer measurement is carried out.

8. The method according to claim 6;
wherein a laser scanning microscope is used for transforming the fluorophores into the excitable state.

9. The method according to Claim 1;
wherein steps b) and c) are repeated for each microscope image for evaluation of a temporal sequence of microscope images containing intensity distributions of fluorescence events of the sample;
wherein the intensity distributions due to diffraction have a respective extent Which corresponds to an extent of a point spread function of the microscope; and
1,wherein the intensity distributions due to diffraction are arranged in each instance inside the microscope images at least predominantly without overlapping.

10. The method according to claim 1;
wherein counter contents are logged, and the counter is initialized in each instance after evaluation of a predetermined quantity of microscope images.

11. The method according to claim 1;
wherein, for step b), a location of a centroid of an intensity distribution of a fluorescence event is determined by means of a compensation computation with sub-diffraction-limited accuracy; or
wherein, for step b), it is ascertained for at least one picture element that a predetermined intensity threshold has been exceeded.

12. The method according to claim 1;
wherein, in case of a fluorophore type which fluoresces reversibly in two colors, incrementing in step c) is carried out only when both fluorescence colors are identified alternately at the same location in successive microscope images in a temporal sequence of microscope images.

13. A control unit configured to implement the method according to claim 1.

14. A microscope comprising:
an illumination beam path with a light source configured to excite at least one type of fluorescent dye in a sample;
a detection beam path including:
a microscope objective; and
a light receiver arranged downstream of the microscope objective; and
a control unit according to claim 13, which is connected to the light source and to the light receiver.

15. A microscope according to claim 14;
wherein the light source is configured to photoswitch a fluorescent dye.

16. A non-volatile information recording medium which is readable by a computer, comprising:
a computer program recorded on the information recording medium;
wherein the computer program includes instructions which cause the computer to implementing the method according to claim 1.

* * * * *